(12) United States Patent
Smith et al.

(10) Patent No.: US 8,070,668 B2
(45) Date of Patent: Dec. 6, 2011

(54) CONTROLLED INFLATION OF A PNEUMATIC L-VAD

(75) Inventors: Robert M. Smith, Grosse Ile, MI (US); Roger W. Snyder, New Braunfels, TX (US); Paul G. DeDecker, Clinton Township, MI (US)

(73) Assignee: L-Vad Technology, Detroit, MI (US)

( * ) Notice: Subject to any disclaimer, the term of this patent is extended or adjusted under 35 U.S.C. 154(b) by 1065 days.

(21) Appl. No.: 11/625,396

(22) Filed: Jan. 22, 2007

(65) Prior Publication Data

US 2007/0173682 A1 Jul. 26, 2007

Related U.S. Application Data

(60) Provisional application No. 60/760,581, filed on Jan. 20, 2006.

(51) Int. Cl.
*A61N 1/362* (2006.01)
(52) U.S. Cl. ............... 600/16; 600/17; 600/18; 623/3.1
(58) Field of Classification Search ............ 600/16–18; 623/3.1
See application file for complete search history.

(56) References Cited

U.S. PATENT DOCUMENTS

| | | | |
|---|---|---|---|
| 4,768,544 A * | 9/1988 | Beam et al. ............ 137/315.04 |
| 4,787,368 A | 11/1988 | Kageyama | |
| 4,969,866 A | 11/1990 | Inagaki | |
| 5,020,516 A | 6/1991 | Biondi et al. | |
| 5,133,744 A | 7/1992 | Ramos Martinez | |
| 5,232,434 A * | 8/1993 | Inagaki et al. ............... 600/16 |
| 5,685,698 A * | 11/1997 | Smoll ........................ 417/50 |
| 5,902,229 A | 5/1999 | Tsitlik et al. | |
| 6,406,458 B1 * | 6/2002 | Tillander ................. 604/147 |
| 6,620,121 B1 | 9/2003 | McCotter | |
| 6,623,420 B2 | 9/2003 | Reich et al. | |
| 6,735,532 B2 * | 5/2004 | Freed et al. ................ 702/50 |
| 7,074,176 B2 * | 7/2006 | Sacristan .................... 600/17 |
| 2005/0245897 A1 * | 11/2005 | Bolduc et al. ............. 604/524 |

* cited by examiner

*Primary Examiner* — Niketa Patel
*Assistant Examiner* — Joseph Stoklosa
(74) *Attorney, Agent, or Firm* — Patent Procurement Services

(57) ABSTRACT

A drive unit to control the peak pressure of air for the inflation of a left ventricular assist system is disclosed. The control of the peak pressure can address the problem of the "kick" experienced by patients when the peak inflation pressure reaches approximately 200 mm Hg. The peak pressure of the air released for the inflation cycle of the system is reduced either by the reduction of the inner diameter of the interconnect line running from the compression tank to the valve manifold or the use of a multi-valve manifold with independently controlled valves and an electronic controller to selectively open and close the valves of the manifold. Either technique, whether used alone or in combination, reduces the peak pressure of the air released for the inflation cycle to below the levels associated with the "kick," while still meeting the operating specifications to properly inflate and deflate the system's blood pump.

6 Claims, 4 Drawing Sheets

CONTROLLED INFLATION OF A PNEUMATIC L-VAD

CROSS-REFERENCE TO RELATED APPLICATIONS

This application claims priority of U.S. Provisional Patent Application Ser. No. 60/760,581 filed Jan. 20, 2006, which is incorporated herein by reference.

FIELD OF THE INVENTION

The present invention relates to an improved system and method for the operation of a pneumatically actuated left ventricular assist device. In particular, the present invention relates to a system and method for controlling the delivery of air to a pump designed to move blood through the arterial tree.

BACKGROUND OF THE INVENTION

Congestive heart failure is a major cause of death and disability in the United States. While some cardiac patients respond to pharmacological therapies, the alternative treatment for a patient who does not respond to conventional therapies is a heart transplantation. Heart transplantations generally require the patient to wait for a donated heart; so as a bridge to a heart transplant, many patients may rely upon mechanical assistance provided by a left ventricular assist device ("LVAD") for temporary assistance, as well as a destination therapy.

A typical prior art LVAD, as shown in FIG. 1, consists of the blood pump 1, an inflatable bladder; an internal conduit 2 connecting the blood pump to the percutaneous access device ("PAD"); the PAD 3, a through-the-skin port that permits power, electrical signals and internal fluid (typically air) to pass between the drive unit and blood pump; and the external drive unit 5, a device powering and controlling the blood pump. The inflatable bladder typically either rings the aorta or is sutured thereto. The PAD 3 allows the implanted blood pump 1 to be operatively connected to or disconnected from the external drive unit 5. To inflate the blood pump 1, pressurized air is supplied from the drive unit compressor (not shown). The air flows from the compressor via an interconnect line through a valve manifold in drive unit 5 to an external drive line 4 running to the PAD 3 and then through the implanted internal drive line 2 to the blood pump 1. Alternatively, an isolation chamber, separating the pressure (or vacuum) source from the air flowing to the pump, can be used to isolate the subcutaneous portion of the pneumatic circuit from the supercutaneous portion.

An integral component of an LVAD system is the controlled inflation of the pneumatic blood pump component of the LVAD. In the CardioVad system made by L. VAD Technology, Inc., there are two types of drive units that control inflation of the blood pump. The first type is the line-powered drive unit ("LDU"). The LDU is run by household current and the power cord severely restricts the patient's mobility. The second type is the wearable drive unit ("WDU"). The WDU, as suggested by its name, is a battery-powered unit worn within a specially designed vest or belt, and allows the patient the mobility not permitted by the LDU.

When WDU trials began with human patients, some patients complained that they felt a sharp, abrupt pain or "kick" in their chest when the blood pump was operating. The origin of the sharp pain was traced to the rapid inflation of the blood pump caused by the initial release of air from the compression tank at the beginning of a pump inflation cycle. Although the precise physiological cause of the pain has not been determined, it is generally attributed to the strain on the aorta and surrounding, interrelated biological features, caused by the inflation of the pump.

The pneumatic design of the WDU allowed the initial release of air to enter the pump at a high pressure, with a peak value of approximately 200 mm Hg. Because of differences between the LDU's closed loop pneumatic design and the WDU's open loop design, the LDU operates with a peak pressure of approximately 175 mm Hg and does not have the "kick" problem of the WDU. Thus, based on clinical experience with these LVADs, a system is desired that can reduce patient pain associated with the "kick," while still meeting all the important operating specifications.

U.S. Pat. No. 5,904,666 to DeDecker and Freed (entitled "Method and Apparatus for Measuring Flow Rate and Controlling Delivered Volume of Fluid Through a Valve Aperture") discloses a technique for estimating the volume of fluid flowing through a valve in a pneumatic LVAD, using a valve having a fixed aperture across which pressure measurements are made. The differential pressure values are used to determine the total volume of fluid passing through the valve. This patent discloses a system for measurement of a volume of air delivered to inflate the blood pump, but discloses nothing to address the problem of regulating the peak pressure of the air exiting the valve to the blood pump to prevent the "kick" problem under all operating conditions.

U.S. Pat. No. 6,042,532 to Freed and Psakhis (entitled "Pressure Control System for Cardiac Assist Device") discloses a control scheme for changing the pressure in the air tank in a pneumatic LVAD so that the blood pump is fully inflated in a desired length of time. This patent discloses the same valve system and flow measurement scheme as disclosed in U.S. Pat. No. 5,904,666, but discloses nothing to address the potential "kick" problems inherent in that system.

U.S. Pat. No. 6,735,532 to Freed, Psakhis and DeDecker (entitled "Cardiovascular Support Control System") discloses control techniques for measuring pneumatic LVAD patient parameters, along with methods for timing the inflation and deflation of the blood pump. This patent discloses the same valve system and flow measurement scheme as disclosed in U.S. Pat. Nos. 5,904,666 and 6,042,532, but discloses nothing to address the potential "kick" problems inherent in that system.

The prior art designs of the drive unit were developed to address problems of optimizing the timing and volume of air delivered for inflation of the blood pump within a wide range of heart rates (e.g. 30 to 180 beats per minute) and responding to fluctuations in the patient's heart rate. However, these known designs do not control the peak pressure of the initial release of air to the blood pump, other than by establishing a maximum value based on the need to avoid rupturing the bladder. The valve controls of the prior art drive units modulate the timing and volume of air for the inflation and deflation cycles, and automatically adjust the timing to compensate for changes in heart rate. None of the prior art discloses any technique for controlling the peak pressure of the initial release of air to the blood pump, to prevent the "kick" problem seen in some drive units. Thus, there is a need in the art for an LVAD pump inflation system that can reduce or eliminate patient discomfort from the inflation "kick" while still meeting all important operating specifications.

SUMMARY OF THE INVENTION

Processes are provided for addressing the "kick" problem by limiting the peak air pressure entering the pump to a level that doesn't cause potential discomfort. In a first process, the valve manifold used to regulate the flow of air exiting the air tank can be composed of at least two multiple valves arrayed in parallel configuration, each of which is independently controlled. With such a valve system, only the required number of valves needs to be opened to inflate the pump. Also, the valves can be opened sequentially to control the maximum pressure of air entering the blood pump. The valve electronic controller is an improvement upon designs using only one large valve or multiple valves which could not be controlled independently, and thus the pressure of the air released from the valve could not be modulated as in the present design.

Another process employs boundary layer fluid mechanics to limit the maximum air pressure. By careful design, the internal diameter and length of the air line connecting the air supply to the blood pump can be selected to limit the maximum air pressure entering the blood pump to a desired value while still meeting important operational conditions, such as inflation time.

By using these techniques, alone or in combination, the peak value of the air pressure of the initial release of air to inflate the LVAD pump can be reduced to comfortable levels, thereby reducing or eliminating the "kick" problem found in the prior art WDUs.

BRIEF DESCRIPTION OF THE DRAWINGS

Preferred features of the present invention are disclosed in the accompanying drawings, wherein similar reference characters denote similar elements throughout the several views, and wherein.

DETAILED DESCRIPTION OF THE PREFERRED EMBODIMENTS

Figure 1:
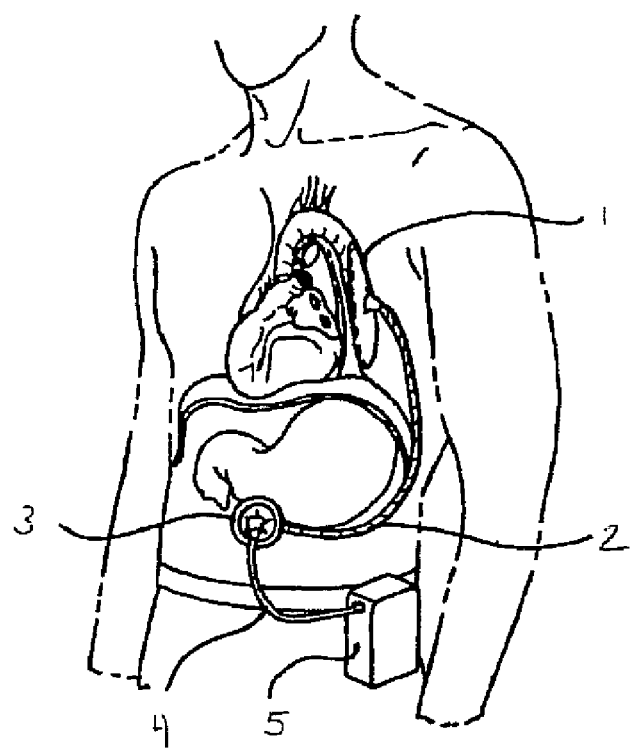
FIG. 1 is a schematic illustration of the major components of a prior art LVAD system.

For convenience, the same or equivalent elements in the various embodiments of the invention illustrated in the drawings have been identified with the same reference numerals. Further, in the description that follows, any reference to either orientation or direction is intended primarily for the convenience of description and is not intended in any way to limit the scope of the present invention thereto.

The present invention relates to techniques for controlling the drive unit of a cardiac assist device in a cardiac patient receiving left ventricular function assistance.

Figure 2:
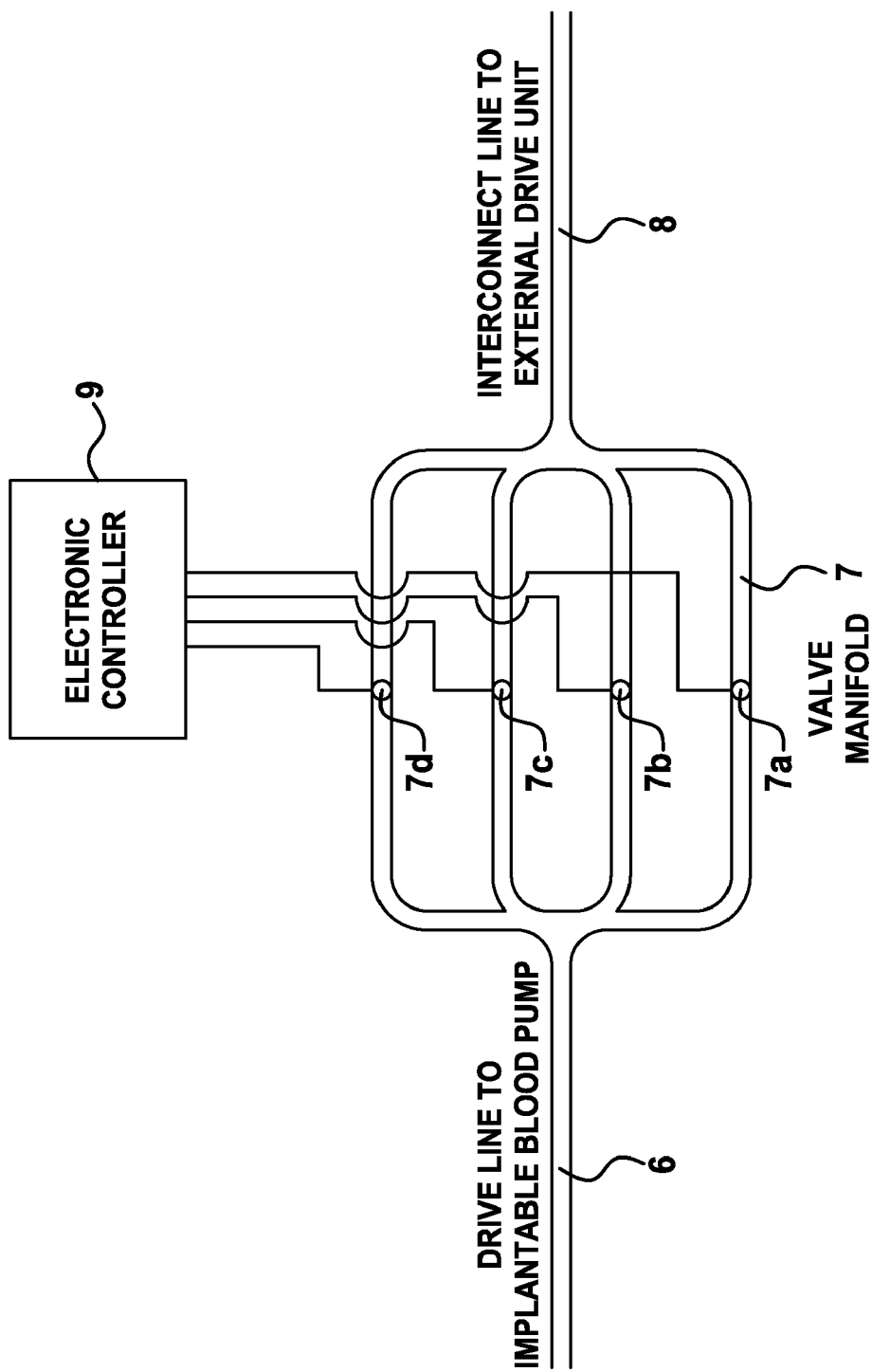
FIG. 2 is a schematic illustration of part of an LVAD system according to the present invention, and includes the interconnect tube, the valve manifold, the electronic controller (of the valve manifold), and the air tube leading to the blood pump.

The invention specifically provides techniques for controlling the pressure of air released by a drive unit to inflate the blood pump of an LVAD to reduce the "kick" problem caused by previous drive unit designs. The major components of the invention are shown in FIG. 2. The interconnect line 6 is a conduit for atmospheric air from the drive unit pressure source (such as a compressor tank (not shown)) to the drive unit valve manifold 7. The drive line 8 is the conduit for air released from the throttling valve manifold to the blood pump (not shown in FIG. 2). Clinical experience has shown that patients experience discomfort when the peak pressure delivered to the pump is around 200 mm Hg, but did not experience pain when the peak pressure was around 160 mm Hg. Thus, the problem was to provide a design which would allow the peak pressure to be reduced to about 160 mm Hg, while still meeting all the other system operating requirements.

Figure 3:
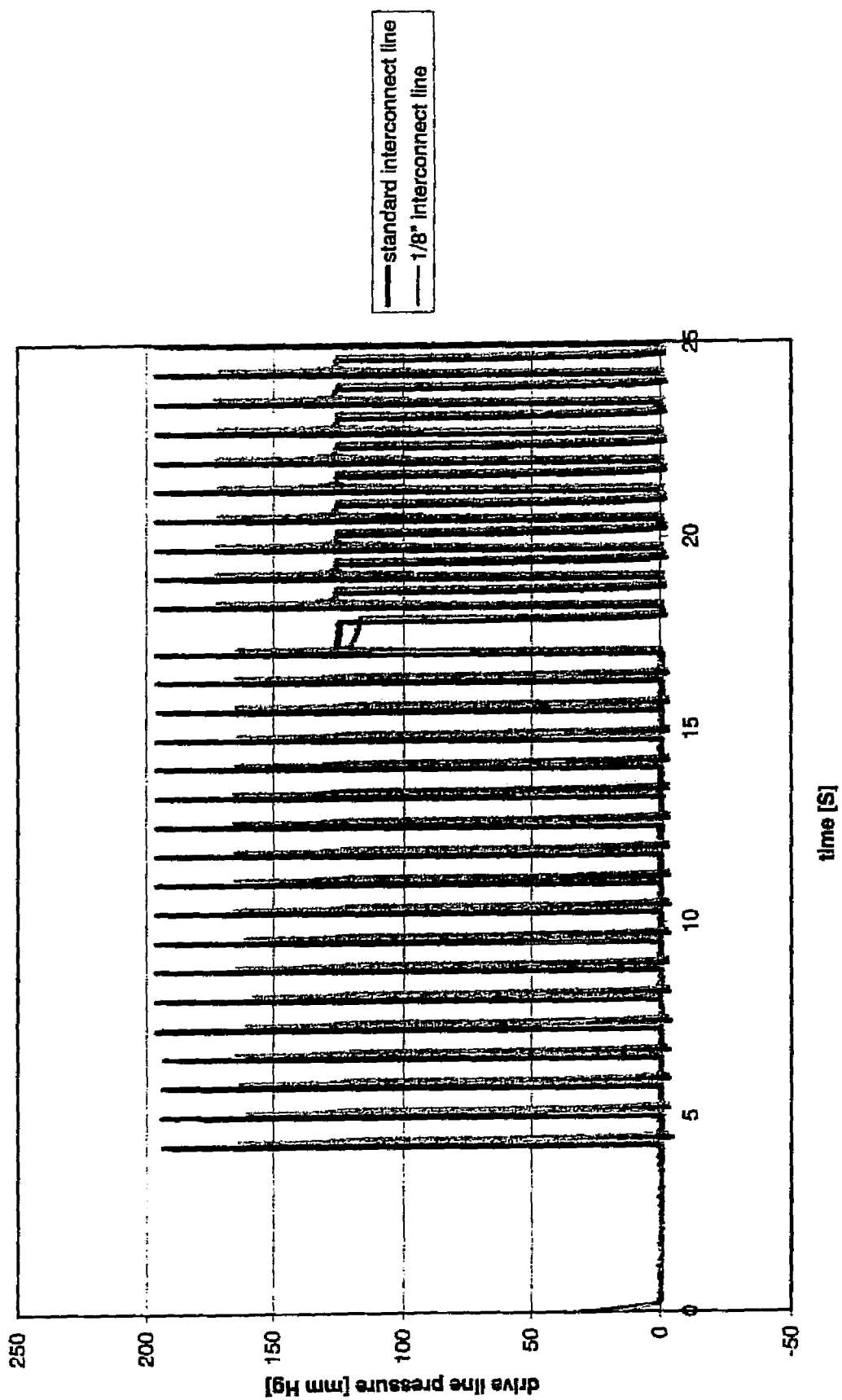
FIG. 3 is a graph showing a time series of air pressure measurements of air exiting the throttling valve of a drive unit with a standard 3/16 inch diameter interconnect line, compared with the pressure of the air exiting a drive unit with a 1/8 inch diameter interconnect line.

The present invention provides for reducing peak air pressure during pump inflation with the use of a smaller internal diameter interconnect line 6 than what would be used based purely on other system considerations, resulting in a comparatively greater percentage of air flow exposed to resistive laminar flow along the interior wall of interconnect line 6 in a smaller internal diameter line, for a given drive line diameter. The line size (internal diameter) must be carefully chosen to be large enough to permit pump inflation and deflation in the required time periods. FIG. 3 shows the reduction in the pressure of air released from the valve manifold to the drive line 8 from a drive unit with an 1/8 inch diameter interconnect line, compared to the pressure released from a drive unit with the standard 3/16 inch interconnect line. The reduction in pressurization ability through line dimension has previously been disfavored. Interconnect line internal diameter (i.d.) is typically between 0.03 and 0.30 inches with pressure profiles readily modeled for a given system using fluid flow dynamic software conventional to the art. Preferably, the i.d. is between 0.08 and 0.25 inches. The initial release of air to the blood pump with a standard interconnect line has a peak pressure of approximately 200 mm Hg, compared to the peak pressure of 160 mm Hg released to the blood pump by a drive unit with an interconnect line of 1/8 inch diameter. It is appreciated that the above description as to drive line internal diameter relates to air pressurization, and that the use of an alternative pressurization fluid having a different root mean square velocity will modify the optimal drive line diameter, yet the ratio of internal diameter decrease to preclude a pressurization kick is consistent with the above diameter ratio for air pressurization.

Figure 4:
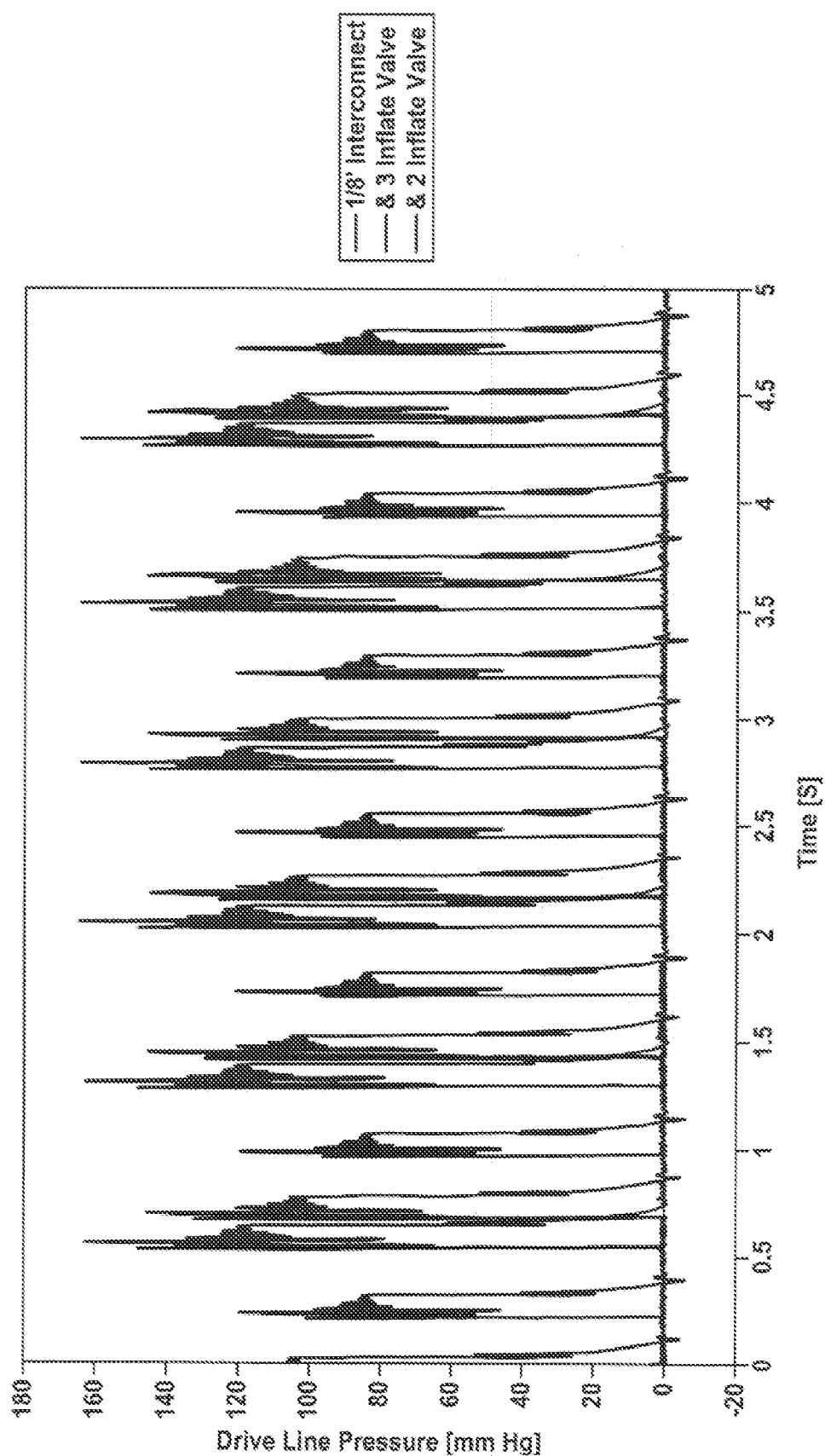
FIG. 4 is a graph showing a time series of air pressure measurements of air exiting the throttling valve of a drive unit with a 1/8 inch interconnect tube with four valves open, compared with a drive unit with a 1/8 inch interconnect tube with three valves open, and a drive unit with a 1/8 inch interconnect tube with two valves open.

Peak blood pump pressure is also reduced through the employ of a valve manifold 7 that includes multiple valves (7a-7d) arranged in parallel. Peak pressure is reduced by having each valve independently controlled by the electronic controller 9, and thus selectively opened and closed. The independent control of the valves permits less than all of the valves to be opened at any given time. While four valves are depicted in FIG. 2, it is appreciated that any number of two or more valves are operative herein. Typical valve numbers are three to seven. The multiple valves of the present invention also create a redundancy that allows the inventive device to function even after a valve failure. Laboratory tests have shown that by only opening some of the valves at the beginning of the inflation cycle, the peak pressure of the air leaving the valve manifold via the air tube can be reduced as shown by FIG. 4. That figure compares the pressure of air released from different open valve configurations. A drive unit using the 1/8 inch diameter interconnect line, and with all four valves open, has an initial air release with a peak pressure of approximately 160 mm Hg. A drive unit with the same interconnect tube, but three of the four valves open, has an initial air release with a peak pressure of approximately 145 mm Hg; and the same drive unit with only two of the four valves open has an initial air release with a peak pressure of approximately 120 mm Hg. The electronic controller 9, which in prior designs modulated the timing and volume of the air released to inflate the blood pump by operating all of the valves identically, is now provided with software modifications to independently control the component valves 7a-7d, to regulate the peak pressure of the initial release of air to the blood pump. Typically peak pressures are maintained between 80 and 160 mg Hg.

The present drive unit design using reduced inner diameter lines or selective valve control, each either alone or in combination, has been found to reduce the pressure of the initial release of air to the blood pump to levels at which patients do not experience the problem of the "kick." The present design uses the fluid dynamics solution of a smaller diameter interconnect line (such as ⅛ inch internal diameter) and multiple, independently controlled valves in a valve manifold, to control the peak pressure caused by the initial release of the air to inflate the blood pump, thereby reducing or eliminating the "kick" problem of prior drive unit designs.

while it is apparent that the illustrative embodiments of the invention discussed above fulfill the objectives stated, it will be appreciated that numerous modifications and other embodiments may be devised by those skilled in the art, while still being covered by the disclosures of the patented invention. Therefore, it will be understood that the appended claims are intended to cover the forgoing—and all other—modifications and embodiments which come within the spirit and scope of the present invention.

The invention claimed is:

1. A process for controlling the pressure profile of air released by a drive unit to inflate an inflatable bladder of an implantable left ventricular assist device pump comprising:

providing the drive unit in fluid communication with the inflatable bladder of the left ventricular assist device pump by way of an interconnect line having an internal diameter;

periodically releasing air from the drive unit to inflate the pump to a peak pressure; and limiting the peak pressure to less than 160 millimeters mercury by opening less than all of a plurality of parallel valves intermediate between said interconnect line and the inflatable bladder of the left ventricular assist device pump at an onset of the periodic release of air so as to control the pressure profile of air released by the drive unit to inflate the pump, wherein air flows through at least two valves of said plurality of valves from the drive unit to the inflatable bladder during said periodic release of air.

2. The process of claim 1 wherein the internal diameter of said interconnect line is between 0.03 and 0.30 inches.

3. The process of claim 1 wherein said plurality of valves is from three to seven valves.

4. The process of claim 1 further comprising opening at least one of said plurality of valves during the periodic release of air and subsequent to the onset.

5. The process of claim 4 further comprising opening all of said plurality of valves during the periodic release of air and subsequent to the onset.

6. The process of claim 1 wherein the peak pressure is between 80 and 160 millimeters mercury.

* * * * *